United States Patent
Tuan

(10) Patent No.: US 10,076,662 B2
(45) Date of Patent: Sep. 18, 2018

(54) PORTABLE ONE-PIECE THERAPEUTICAL APPARATUS WITH DUAL HEATING AND LOW-FREQUENCY TREATMENT FUNCTIONS

(71) Applicant: HIVOX BIOTEK INC., New Taipei (TW)

(72) Inventor: Wei Tuan, Taipei (TW)

(73) Assignee: HIVOX BIOTEK INC., New Taipei (TW)

( * ) Notice: Subject to any disclaimer, the term of this patent is extended or adjusted under 35 U.S.C. 154(b) by 22 days.

(21) Appl. No.: 14/922,560

(22) Filed: Oct. 26, 2015

(65) Prior Publication Data

US 2017/0113039 A1 Apr. 27, 2017

(51) Int. Cl.
  *A61N 1/36* (2006.01)
  *A61N 1/04* (2006.01)
  *A61F 7/00* (2006.01)

(52) U.S. Cl.
  CPC .......... *A61N 1/36021* (2013.01); *A61F 7/007* (2013.01); *A61N 1/0492* (2013.01); *A61F 2007/0071* (2013.01); *A61F 2007/0078* (2013.01); *A61F 2007/0093* (2013.01)

(58) Field of Classification Search
  CPC ........................ A61N 1/36021; A61N 1/0492
  See application file for complete search history.

(56) References Cited

U.S. PATENT DOCUMENTS

| 6,415,177 B1 * | 7/2002 | Tuan ..................... A61H 39/002 607/3 |
| 8,463,388 B2 | 6/2013 | Wei |
| 2005/0043655 A1 * | 2/2005 | Schenck ................ A61H 23/02 601/15 |
| 2010/0228304 A1 * | 9/2010 | Kriksunov .............. A61F 7/007 607/3 |

FOREIGN PATENT DOCUMENTS

| TW | 201117850 A | 6/2011 |
| TW | M480998 U | 7/2014 |

* cited by examiner

*Primary Examiner* — George Evanisko
(74) *Attorney, Agent, or Firm* — Muncy, Geissler, Olds & Lowe, P.C.

(57) ABSTRACT

A portable one-piece therapeutical apparatus with dual heating and low-frequency treatment functions includes a main unit having an accommodating space and a patch portion; a control means installed in the accommodating space and including a printed circuit board assembly with an operating component for controlling low-frequency pulses and a heating operation, an electrical connector installed at the front of the printed circuit board assembly for charging a battery and reading, writing and transmitting data; at least one heating means installed at the main unit and electrically coupled to the printed circuit board assembly for producing a heating effect; at least one low-frequency electrode layer disposed under the patch portion and electrically coupled to the printed circuit board assembly for transmitting low-frequency pulses; and a battery installed in the accommodating space and directly and electrically coupled to the printed circuit board assembly for supplying power to the patch therapeutical apparatus.

4 Claims, 6 Drawing Sheets

PORTABLE ONE-PIECE THERAPEUTICAL APPARATUS WITH DUAL HEATING AND LOW-FREQUENCY TREATMENT FUNCTIONS

TECHNICAL FIELD

The technical field relates to a therapeutical apparatus for medical treatment, and more particularly to a portable multi-functional therapeutical apparatus with both heating and low-frequency treatment functions, and the apparatus adopts the structure of wireless wires to provide features of easy portability and good power saving effect.

BACKGROUND

At present a low frequency therapeutical apparatus is commonly used for treating and soothing different types of pain, since the low frequency therapeutical apparatus is capable of emitting electronic pulse waveforms including dense waves, sparse waves, sparse-dense waves, sawtooth waves, intermittent waves, etc with the effect of treating and soothing pains. For example, dense waves are generally used for pain relief, sedation, sore muscle soothing, blood vessel spasm, acupuncture anesthetic, etc; sparse waves are generally used for treating atrophy diseases, and muscle, joint, ligament, tendon injuries, etc; sparse-dense waves in a waveform of alternate sparse waves and dense waves are generally used for pain relief, contusion, joint periarthritis, blood circulation disorder, sciatica, facial paralysis, weak muscle, partial frostbite, etc; sawtooth waves with pulse in sawtooth shape and changes of undulating waves are generally used for electric simulation of phrenic nerves for artificial respiration, rescue for respiratory failure, neuromuscular excitability, blood circulation improvement, etc; and intermittent waves in form of sparse waves which are continuous and discontinuous with a rhythm and generally used for treating atrophy, paralysis, muscular electric gymnastic training, etc.

As to physical therapy, fomentation is generally used for treating pains and promoting rehabilitation to achieve the effects of raising the temperature of the affected tissues, accelerating blood circulation, promoting healing speed, and relieving pains. According to researches, thermotherapy at least has the effects of: (1) relieving pains; (2) reducing muscle spasm; (3) relieving stiff joints; (4) improving the ductility of collagen to improve joint activity; and (5) improving blood circulation.

With reference to FIG. 1 for a conventional low frequency therapeutical apparatus (as disclosed in Patent Application No. TW201117850A1), the apparatus is a one-piece electronic low-frequency pulse patch 90 comprising a soft upper casing 91, a hollow support casing 92, a coupled output conductive soft film 93, a control circuit unit 94, a base 95, a power supply unit 96 and a lower casing 97; wherein the power supply unit 96 and a control circuit unit 94 capable of generating current pulses of anode and cathode are concealed therein to form a one-piece waterproof seamless structure which is used as an automatic sticking patch device for outputting low-frequency pulses and applicable in various electronic patches for treating and soothing human pains.

Although the conventional one-piece electronic low-frequency pulse patch can achieve the effect of treating and soothing human pains, it still has the following drawbacks. The electronic low-frequency pulse patch 90 just has the effect of an electronic pulse waveform without the fomentation effect of a heating patch, and it does not provide the function of individual or alternate heating and low-frequency pulses, so that the therapeutical effect is limited. Obviously, the conventional one-piece electronic low-frequency pulse patch requires improvements.

In addition, a heater with the fomentation effect is disclosed in R.O.C. Pat. No. M480998, the heater consumes much electric power, so that the heater must be electrically coupled to an alternate current (AC) adapter having an input terminal connected to the mains power and the heater is equipped with a thermostat, and such heater is inconvenient to carry, and a patient has to stay at a fixed position and cannot move freely. Therefore, it is a main subject for related manufacturers to overcome the aforementioned drawbacks of the conventional electronic low-frequency treatment apparatus and thermotherapy apparatus.

In view of the drawbacks and poor structural design of the conventional electronic low frequency therapeutical apparatus and thermotherapy apparatus, the discloser of this disclosure conducted extensive researches and experiments, and finally developed a portable power-saving therapeutical apparatus with both heating and low-frequency treatment functions without being limited by a power cable of a power supply to overcome the drawbacks and problems of the prior art.

SUMMARY

Therefore, it is a primary objective of this disclosure to provide a portable one-piece therapeutical apparatus with both heating and low-frequency treatment functions, and the therapeutical apparatus is provided for better treatment and pain relief by individual or alternate effects.

Another objective of this disclosure is to provide a therapeutical apparatus having an electronic patch with both heating and low-frequency treatment functions without being limited by the power cable of a cable power supply, and the therapeutical apparatus has excellent portability and power saving and enhances the scope of applicability and competitiveness of the product.

To achieve the aforementioned objectives, this disclosure provides a portable one-piece therapeutical apparatus with dual heating and low-frequency treatment functions, comprising: a main unit, being in a one-piece form and including a main body portion and a patch portion extended separately and outwardly from both sides of the main body portion, and the main body portion having an accommodating unit, and the accommodating unit having an accommodating space; a control means, installed in the accommodating space, and including a printed circuit board assembly, having an operating component installed on the printed circuit board assembly for controlling heating and low-frequency pulse; at least one heating means, installed at a position of a middle layer of the patch portion, and each including a heating plate electrically coupled to the printed circuit board assembly for producing a heating effect; at least one low-frequency electrode layer, disposed under the heating means, and including a base layer, a low-frequency circuit pattern disposed under the base layer and electrically coupled to the printed circuit board assembly for transmitting a low frequency output; and a battery, installed in the accommodating space, and directly and electrically coupled to the printed circuit board assembly for supplying power to the therapeutical apparatus.

To achieve the aforementioned and other objectives, this disclosure further provides a portable one-piece therapeutical apparatus with dual heating and low-frequency treatment functions, comprising: a main unit, being in a one-piece form and including a main body portion and a patch portion extended separately and outwardly from both sides of the main body portion, and the main body portion having an accommodating unit, and the accommodating unit having an accommodating space; a control means, installed in the accommodating space, and including a printed circuit board assembly, having an operating component installed on the printed circuit board assembly for controlling heating and low-frequency pulse; a heating means, installed under the main body portion, and including a heating plate, and the heating plate having a heating circuit pattern formed thereon and electrically coupled to the printed circuit board assembly for producing a heating effect; at least one low-frequency electrode layer, disposed at the patch portion, and electrically coupled to the printed circuit board assembly for transmitting a low frequency output; and a battery, installed in the accommodating space, and directly and electrically coupled to the printed circuit board assembly for supplying power to the therapeutical apparatus.

In the aforementioned apparatus, the accommodating space includes a port space at the front of the accommodating space, a connector cover installed at the top of the port space and coupled to the display cover, an electrical connector disposed at the front of the printed circuit board assembly and provided for charging a battery and reading, writing and transmitting data.

In the aforementioned apparatus, the patch portion is a silicone plate having an UP key or a DOWN key disposed at an end of the patch portion away from the main body portion, and an attaching layer is formed under the main body portion.

In the aforementioned apparatus, the control means further includes an upper casing and a lower casing for covering and protecting the printed circuit board assembly.

In the aforementioned apparatus, the battery is a rechargeable battery.

In the aforementioned apparatus, the battery is charged by a non-contact electromagnetic method.

In the aforementioned apparatus, the electrical connector supports the USB specification.

In the aforementioned apparatus, a display cover is formed at the top of the accommodating space, and the display cover has a plurality of switches and a plurality of display windows formed thereon, and the switch electrically is coupled to the control means, and the switch is a starter switch or a heating switch.

In the aforementioned apparatus, the heating plate is made of a resistive adhesive layer, a carbon fiber or an electric heating plate.

In the aforementioned apparatus, the resistive adhesive layer is printed with a silver paste to form a heating circuit pattern, and the heating circuit pattern is electrically coupled to the printed circuit board assembly.

In the aforementioned apparatus, a diffuser is installed above the heating circuit pattern layer and made of graphite.

In the aforementioned apparatus, the low-frequency electrode layer includes a base layer, and the base layer is made of a PET material, and a low-frequency circuit pattern is formed under the base layer, and the low-frequency circuit pattern is printed with a silver ink, a carbon ink, or any other conductive material to form a conducting circuit.

In the aforementioned apparatus, a distribution layer is disposed under the low-frequency circuit pattern and formed by an insulated oil printing process for preventing any unnecessary electrode output.

In the aforementioned apparatus, the control means includes a wireless transceiver unit installed therein and operated with a wireless remote controller for displaying various controls and operations.

This disclosure will become clearer in light of the following detailed description of an illustrative embodiment of this invention described in connection with the drawings.

DESCRIPTION OF THE PREFERRED EMBODIMENTS

Figure 1:
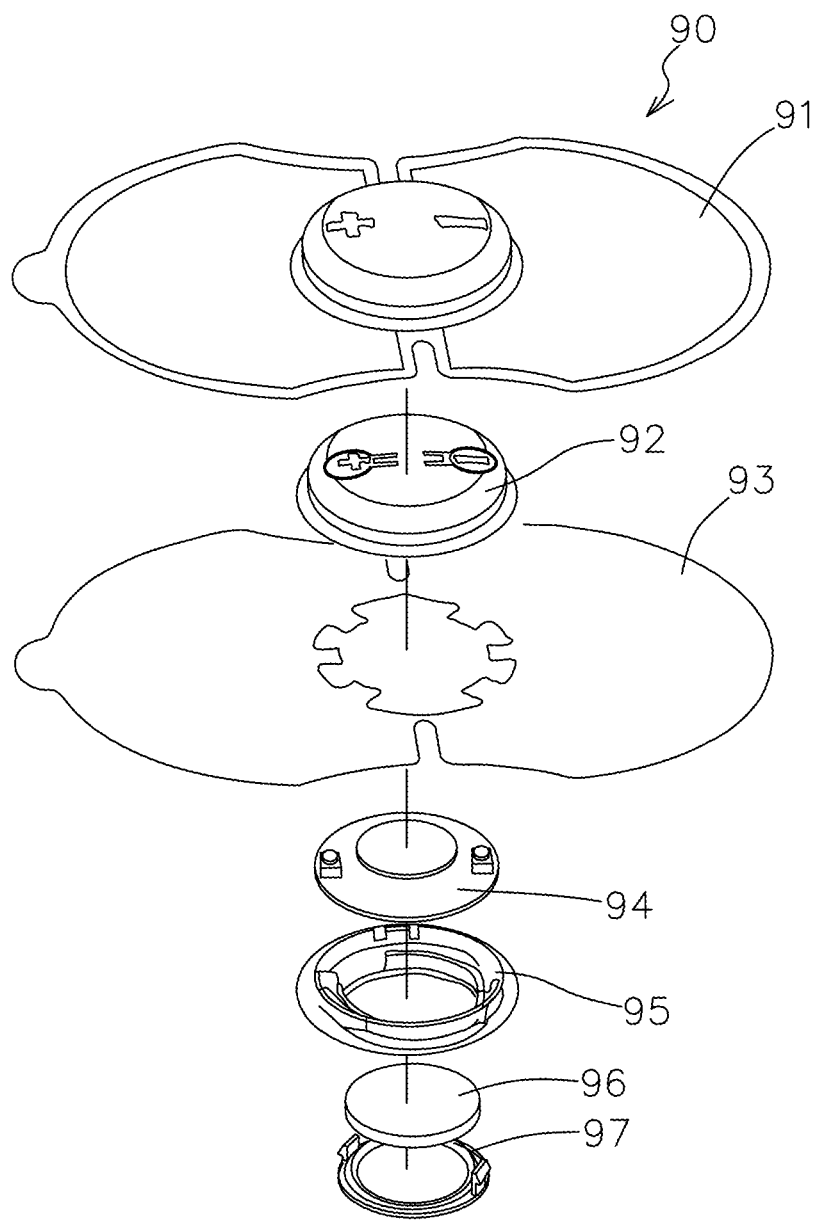
FIG. 1 is a schematic view of a conventional low frequency therapeutical apparatus.
Figure 2:
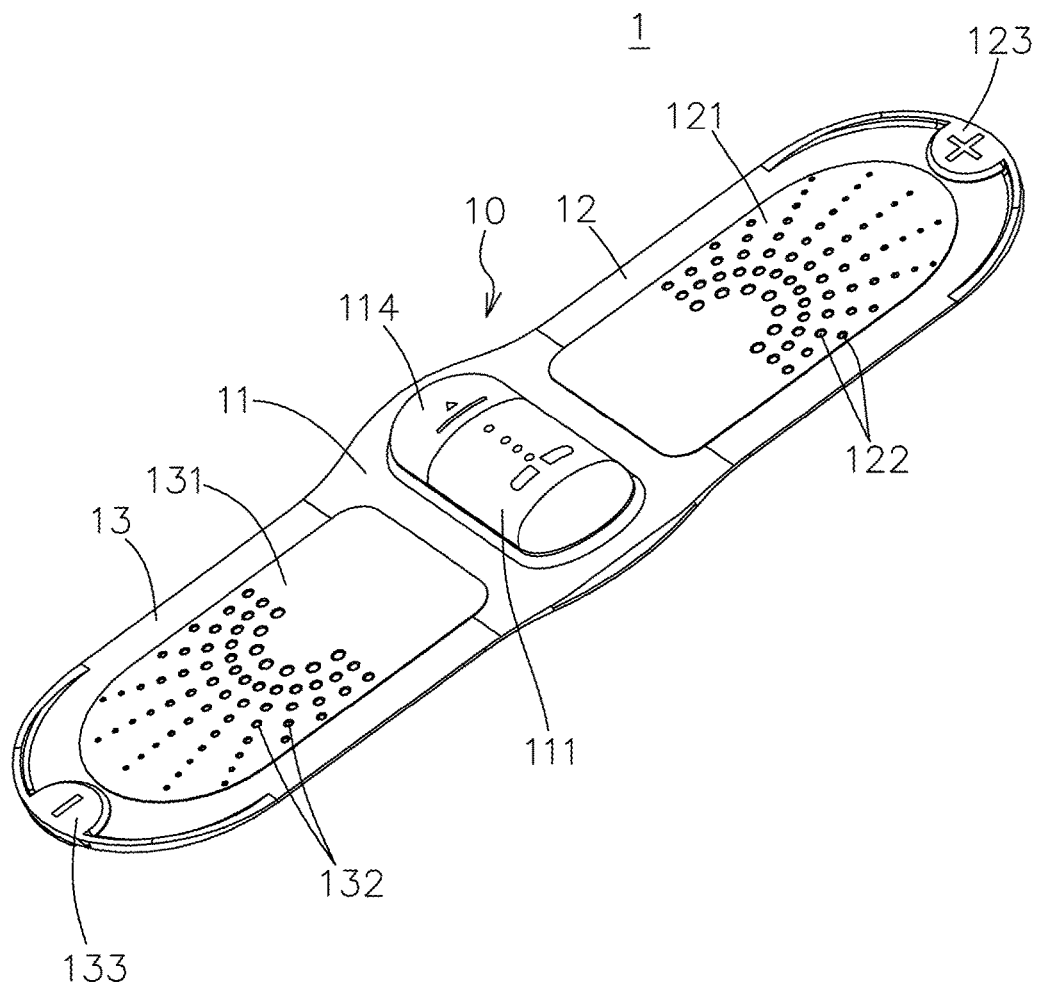
FIG. 2 is a perspective view of a first preferred embodiment of this disclosure.
Figure 3:
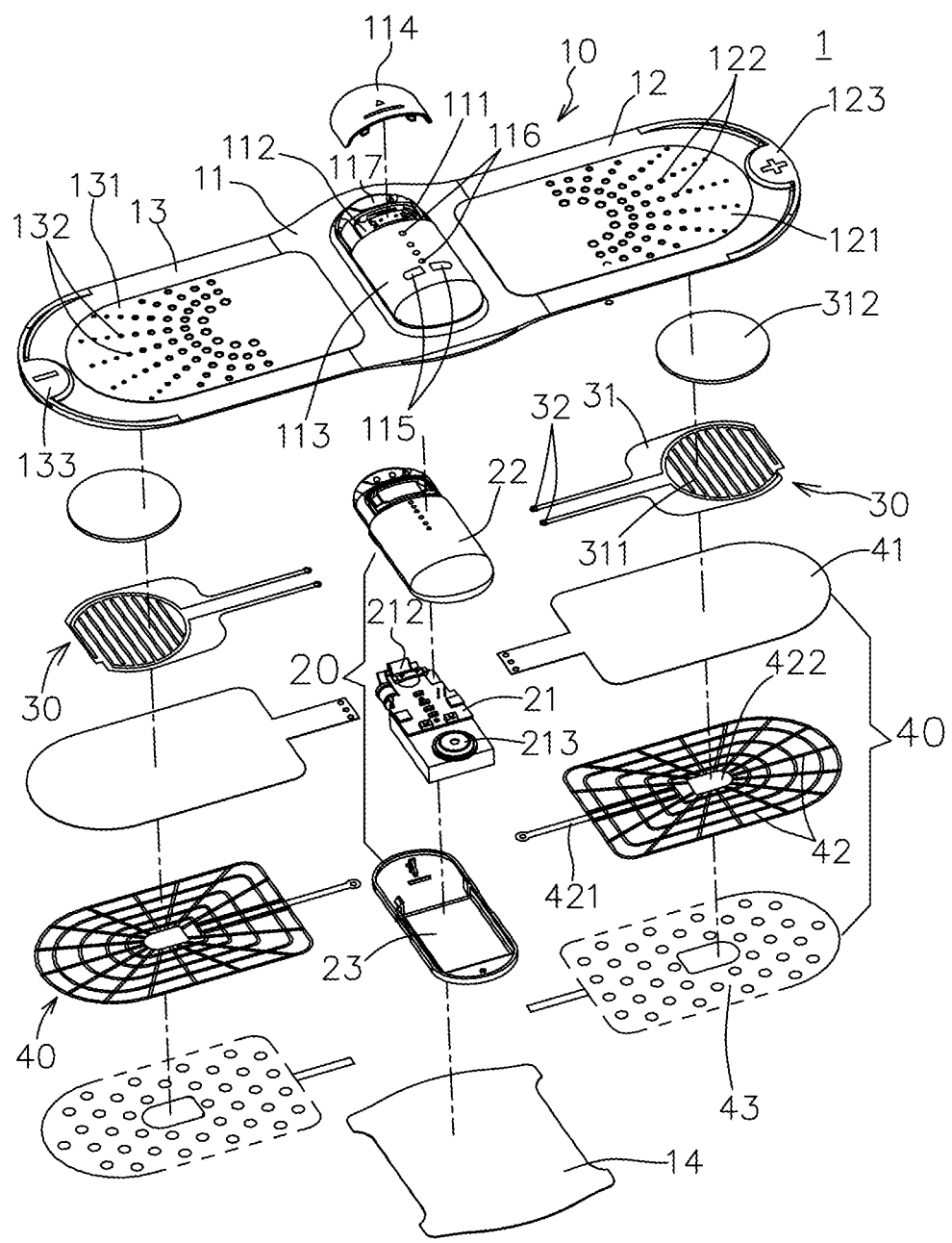
FIG. 3 is an exploded view of the first preferred embodiment of this disclosure.

With reference to FIGS. 2 and 3 for the perspective view and the exploded view of a portable one-piece therapeutical apparatus with dual heating and low-frequency treatment functions in accordance with the first preferred embodiment of this disclosure respectively, these figures are simplified schematic figures provided for the purpose of illustrating the basic structure of this disclosure only, and they are not drawn according to the actual shape, size, and proportion of the apparatus, and thus the scope of this disclosure is not limited by the illustration of these figures. In FIGS. 2 and 3, the one-piece patch therapeutical apparatus 1 of this disclosure comprises a main unit 10, a control means 20, two heating means 30 and two low-frequency electrode layers 40, wherein the main unit 10 is in a one-piece form and includes a main body portion 11 and a patch portion 12 extended separately and outwardly from both sides of the main body portion 11, and the main body portion 11 includes an accommodating unit 111 having an accommodating space 112, and a display cover 113 formed at the top of a substantially middle position of the accommodating space 112, and the display cover 113 has two switches 115 and a plurality of display windows 116 formed thereon, and the two switches 115 are electrically coupled to the control means 20 and at least include a starter switch and a heating switch, and the plurality of display windows 116 is provided for displaying various using statuses. In addition, the front of the accommodating space 112 (in a direction indicated in FIG. 3) has a port space 117, and a connector cover 114 is disposed at the top of the port space 117 and connected to the display cover 113. The patch portions 12, 13 are silicone plates (but this disclosure is not limited to silicone plates only) having a heat dissipating area 121 and a heat dissipating area 131 defined thereon, and both heat dissipating areas 121, 131 have a plurality of heat dissipating holes 122, 132 respectively, and an UP key 123 and a DOWN key 133 are disposed at ends of the patch portions 12, 13 away from the main body portion 11 for controlling and adjusting the supply of voltage (or current). In addition, an attaching layer 14 is disposed under the main body portion 11, and the attaching layer 14 may be a silicone layer attached onto skin and provided for positioning the patch therapeutical apparatus 1.

The control means 20 is installed in the accommodating space 112 of the main body portion 11, and the control means 20 includes a printed circuit board assembly (PCBA) 21, an upper casing 22 and a lower casing 23, wherein the printed circuit board assembly 21 has an operating component (not labeled) for controlling the heating and low-frequency pulse, an electrical connector 212 (which is a USB electrical connector in this preferred embodiment) installed at the front of the printed circuit board assembly 21 and disposed at the port space 117 for charging a charging and reading, writing, and transmitting data, and a battery 213 installed at the rear of the printed circuit board assembly 21. In a preferred embodiment, the battery 213 is a rechargeable battery installed in the accommodating space 112 and electrically coupled to the printed circuit board assembly 21 for supplying power to the therapeutical apparatus, and the battery 213 may be charged through an electrical connector 212 or by a non-contact electromagnetic method, and the upper casing 22 and the lower casing 23 are used for covering and protecting the printed circuit board assembly 21 and the integrated upper casing 22 and lower casing 23 are installed in the accommodating space 112.

The two heating means 30 are the positions of the middle layer of the patch portions 12, 13, and each heating means 30 has a heating plate 31 (which is a resistive adhesive layer in this preferred embodiment. This disclosure is not limited to such arrangement only, but carbon fiber or electric heating plate may be used instead), and the heating plate 31 is printed with a silver paste to form a heating circuit pattern 311, and the heating circuit pattern 311 includes an electrical contact terminal 32 electrically coupled to the printed circuit board assembly 21 for producing a heating effect, and a diffuser 312 may be attached onto the top of the heating circuit pattern 311 (in the direction indicated in the figure), wherein the diffuser 312 is made of graphite and provided for diffusing the heat generated by the heating circuit pattern 311 and preventing the heat from being concentrated at a position to facilitate the heating operation.

The low-frequency electrode layer 40 is disposed under the heating means 30 and includes a base layer 41 made of a PET material; a low-frequency circuit pattern 42, installed under the base layer 41, and including a low-frequency circuit contact terminal 421 coupled to the printed circuit board assembly 21 and disposed at the middle portion 422 of the low-frequency circuit pattern 42, and the low-frequency circuit contact terminal 421 being electrically coupled to the printed circuit board assembly 21, wherein the low-frequency circuit pattern 42 under the base layer 41 is printed with a silver ink, a carbon ink, or any other conductive material to form a conducting circuit in an appropriate implementation mode; a distribution layer 43, disposed under the low-frequency circuit pattern 42, wherein the distribution layer 43 under the low-frequency circuit pattern 42 and the base layer 41 is formed by an insulated oil printing process in an appropriate implementation mode, and the purpose of the distribution layer 43 is to prevent any unnecessary electrode output in order to distribute current uniformly. In addition, the bottom of the distribution layer 43 further has a carbon ink layer (not shown in the figure) and attached and contacted to skin for performing a low frequency output of the low-frequency electrode layer 40.

Figure 4:
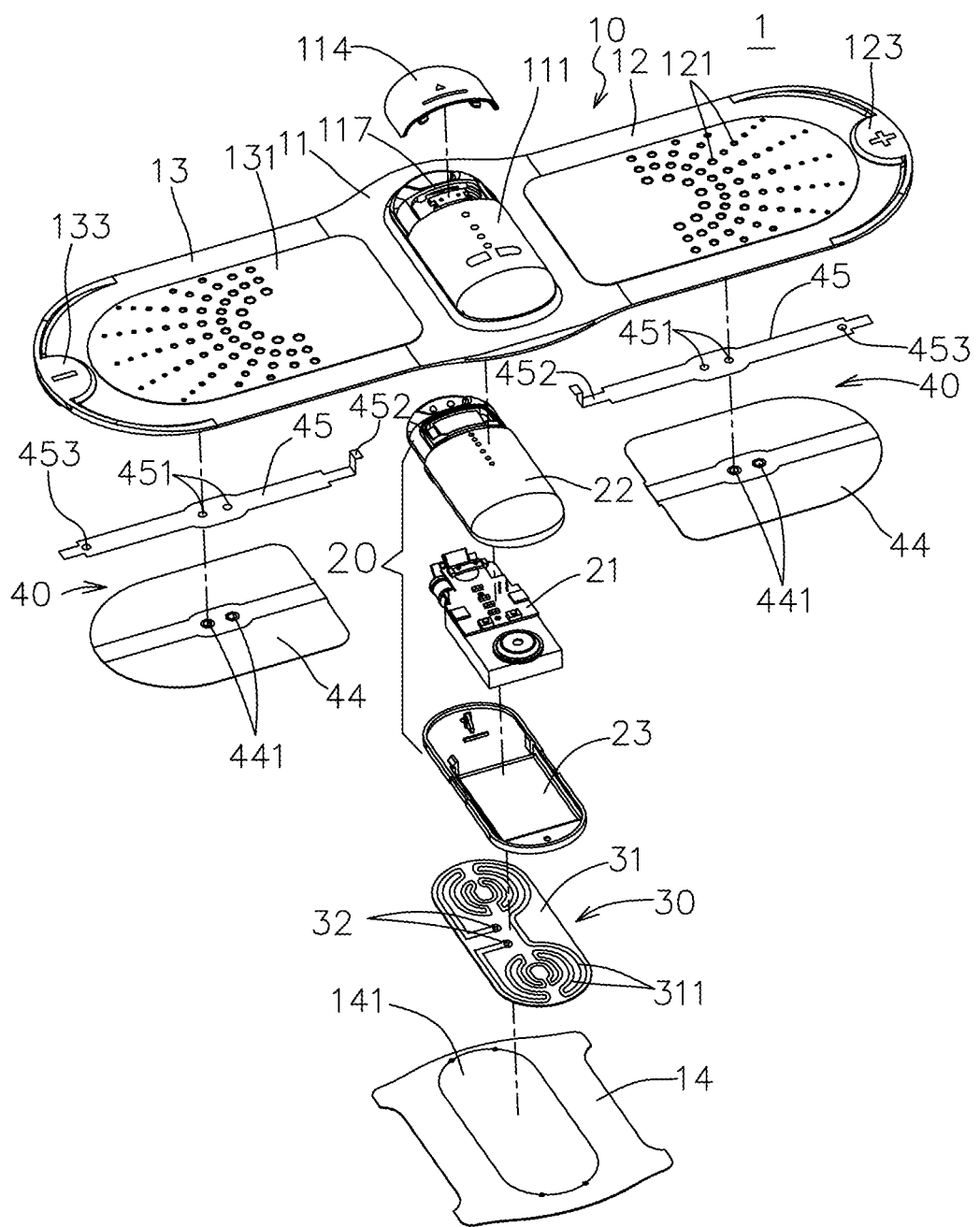
FIG. 4 is a perspective view of a second preferred embodiment of this disclosure.

With reference to FIG. 4 for a portable one-piece therapeutical apparatus with dual heating and low-frequency treatment functions in accordance with a second preferred embodiment of this disclosure, the second preferred embodiment has a slight modification added to the basic structure of the first preferred embodiment, and the second embodiment also comprises a main unit 10, being in a one-piece form and including a main body portion 11 and a patch portion 12 and a patch portion 13 respectively and outwardly extended from both sides of the main body portion 11, wherein the difference between the first and second preferred embodiments resides on that the second preferred embodiment comprises a heating means 30, installed at the main body portion 11 (or under the main body portion 11 of this preferred embodiment, and including a heating plate 31 (which is a resistive adhesive layer in this preferred embodiment, and this disclosure is not limited to such arrangement only, but a carbon fiber or an electric heating plate may be used instead), and the heating plate 31 having a heating circuit pattern 311 formed thereon and the heating circuit pattern 311 having an electrical contact terminal 32 electrically coupled to the printed circuit board assembly 21 for producing a heating effect, and the attaching layer 14 being disposed under the heating circuit pattern 311 and having a carrying portion 141 for carrying and positioning the heating circuit pattern 311; two low-frequency electrode layers 40, disposed under the patch portions 12, 13 respectively and including a conductive rubber layer 44, a positioning portion 441 disposed on the conductive rubber layer 44, an output control wire 45 disposed above the conductive rubber layer 44 and positioned by a positioning portion 451 at the positioning portion 441 of the conductive rubber layer 44, and the output control wire 45 having an inner electrode contact terminal 452 and an outer electrode output terminal 453, and the electrode contact terminal 452 being electrically coupled to the printed circuit board assembly 21, and the electrode output terminal 453 being provided for transmitting a low-frequency pulse output to perform a low-frequency treatment.

Figure 5:
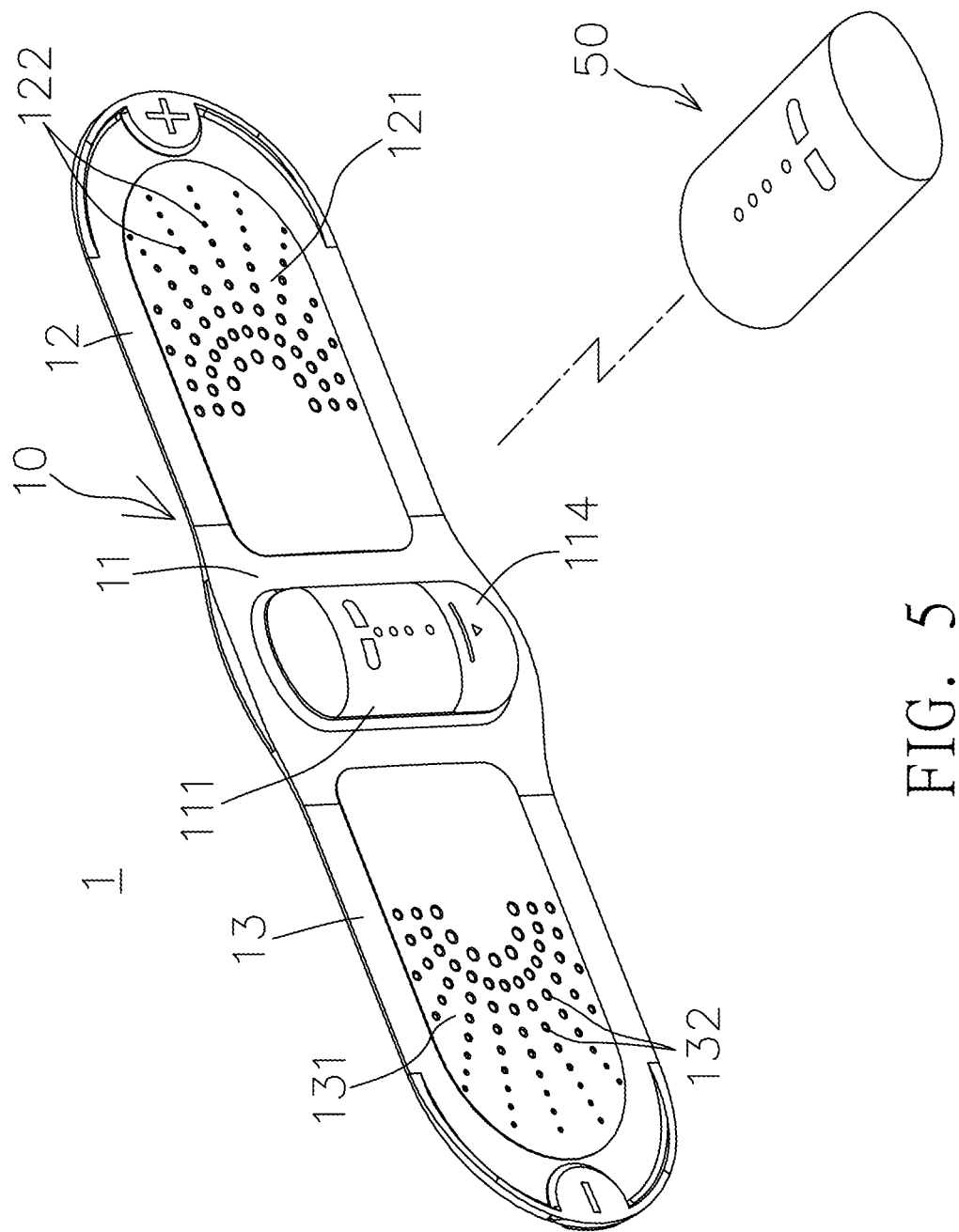
FIG. 5 is a schematic view of a wireless control system of this disclosure.

With reference to FIG. 5 for a schematic view of a wireless control system of a portable one-piece therapeutical apparatus with dual heating and low-frequency treatment functions in accordance with this disclosure, the patch therapeutical apparatus 1 comprises a wireless transceiver unit (not shown in the figure) installed in the control means 20, so that the patch therapeutical apparatus 1 may be operated with a wireless remote controller 50 to carry out a heating process of the heating means 30 and perform a low-frequency treatment by the low-frequency electrode layer 40, and the wireless remote controller 50 may display various controls and operations of the patch therapeutical apparatus 1, and such control operation is especially applicable for a hard-to-reach portion of a human body and the control operation is very convenient.

Figure 6:
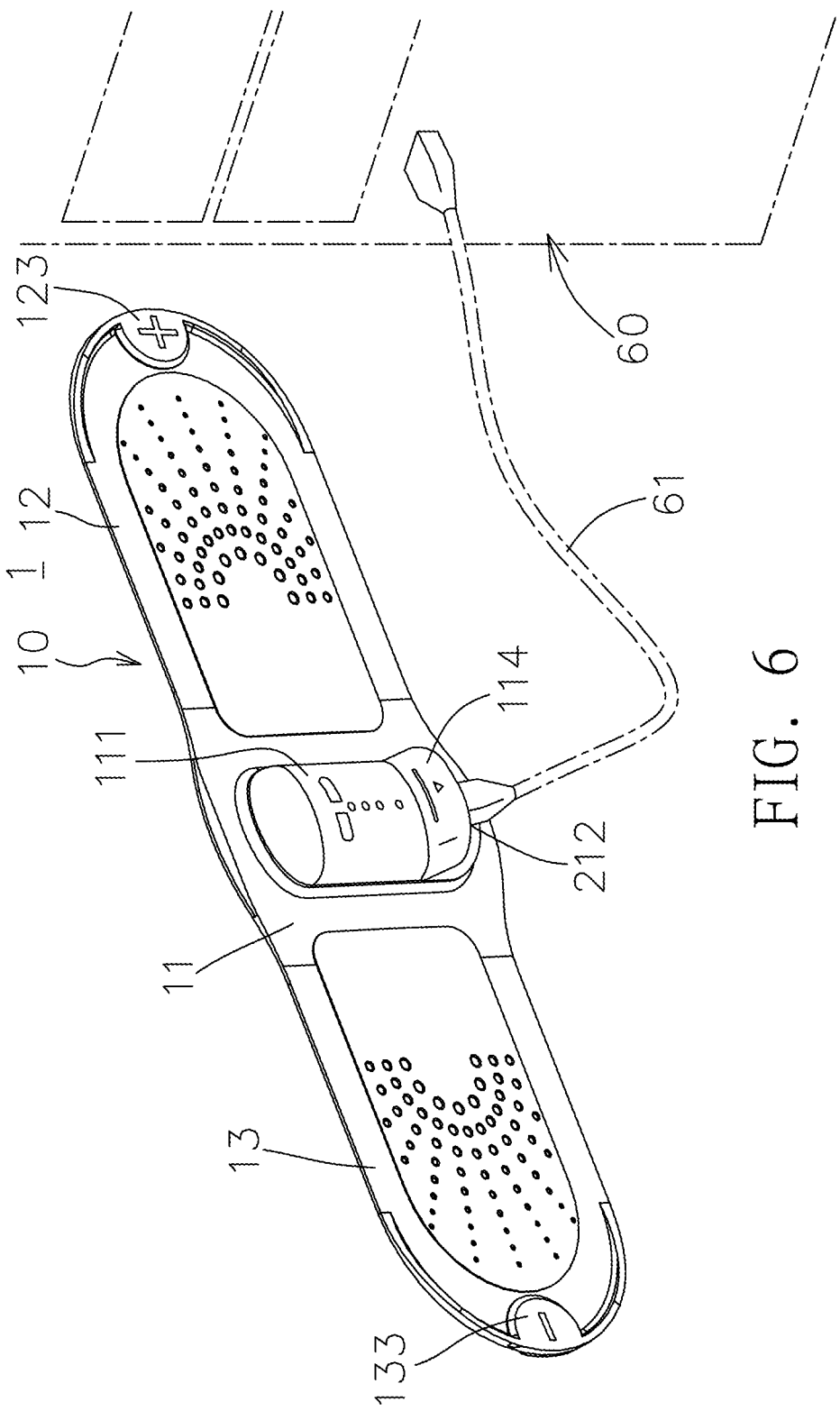
FIG. 6 is a schematic view of a cable control system of this disclosure.

With reference to FIG. 6 for a schematic view of a cable control system of a portable one-piece therapeutical apparatus with dual heating and low-frequency treatment functions in accordance with this disclosure, the patch therapeutical apparatus 1 may be connected to an electrical wire 61 which is plugged into the electrical connector 212 (such as a USB connector), and the other end of the electrical wire 61 is connected to a computer 60, so that the patch therapeutical apparatus 1 and the computer 60 may transmit data with one another, or charge batter of the patch therapeutical apparatus 1, and such applications may use the computer 60 to control and operate the patch therapeutical apparatus 1, and such control and operation method is especially applicable for a hard-to-reach portion of a human body and the control operation can be displayed conveniently.

In the aforementioned cable and wireless control systems of the patch therapeutical apparatus 1, the operating procedure is easy to follow or prepared conveniently by customized software, and this disclosure further provides the cloud application of interactive APP by using a wireless transceiver unit of the control means 20, so as to provide excellent performance and management.

In summation of the description above, the portable one-piece therapeutical apparatus with dual heating and low-frequency treatment functions in accordance with this disclosure provides a multiple of functions including the heating and low-frequency treatment functions which can be used individually or alternately to provide a better treatment or pain relief effect. In addition, the electronic patch of this disclosure provides a multiple of functions while having the advantages of excellent portability and power saving effect and improving the scope of applicability, performance and competitiveness of the product.

What is claimed is:

1. A portable one-piece therapeutical apparatus with dual heating and low-frequency treatment functions, comprising:
    a main unit, being in a one-piece form from injection molded and including a main body portion and patch portions extended separately and outwardly from both sides of the main body portion, and the main body portion having an accommodating unit, and the accommodating unit having an accommodating space;
    a control means, installed in the accommodating space, and including a printed circuit board assembly, having an operating component installed on the printed circuit board assembly for controlling heating and low-frequency pulse;
    a heating means, installed under the main body portion, and including a heating plate, and the heating plate having a heating circuit pattern formed thereon and the heating circuit pattern having an electrical contact terminal electrically coupled to the printed circuit board assembly for the controlling of the heating, and an attaching layer being disposed under the heating circuit pattern and having a carrying portion being undercut shape for carrying and positioning the heating circuit pattern;
    at least two low-frequency electrode layers, disposed under the patch portions respectively and each layer including a conductive rubber layer, a positioning portion disposed on the conductive rubber layer, an output control wire disposed above the conductive rubber layer the wire having and positioned by a positioning portion at the positioning portion of the conductive rubber layer, and the output control wire having an inner electrode contact terminal and an outer electrode output terminal, and the electrode contact terminal being electrically coupled to the printed circuit board assembly, and the electrode output terminal being provided for transmitting the low-frequency pulse output to perform a low frequency treatment; and
    a battery, installed in the accommodating space, and directly and electrically coupled to the printed circuit board assembly for supplying power to the therapeutical apparatus.

2. The portable one-piece therapeutical apparatus with dual heating and low-frequency treatment functions according to claim 1, wherein the accommodating space has a display cover formed at the top of the accommodating space, and the display cover has a plurality of switches and a plurality of display windows disposed thereon, and wherein one switch of the plurality of switches is electrically coupled to the control means and is a starter switch or a heating switch.

3. The portable one-piece therapeutical apparatus with dual heating and low-frequency treatment functions according to claim 2, wherein the accommodating space includes a port space at the front of the accommodating space, a connector cover installed at the top of the port space and coupled to the display cover, an electrical connector disposed at the front of the printed circuit board assembly and provided for charging the battery and reading, writing and transmitting data.

4. The portable one-piece therapeutical apparatus with dual heating and low-frequency treatment functions according to claim 1, wherein the control means includes a wireless transceiver unit installed therein and a wireless remote controller operating with the wireless transceiver unit to display various control and operations.

* * * * *